United States Patent [19] [11] 4,300,576
van der Loo et al. [45] Nov. 17, 1981

[54] SMOKING ARTICLES CONTAINING THAUMATIN OR MONELLIN

[75] Inventors: Henricus E. van der Loo; Charles Wiener, both of Middletown, N.Y.; John D. Higginbotham, Reading, England

[73] Assignee: Talres Development (N.A.) N.V., Netherlands Antilles

[21] Appl. No.: 899,113

[22] Filed: Apr. 24, 1978

[30] Foreign Application Priority Data

Apr. 26, 1977 [GB] United Kingdom ............... 17334/77
Jan. 30, 1978 [GB] United Kingdom ................. 3719/78

[51] Int. Cl.³ .......................... A24B 15/30; A24B 3/12
[52] U.S. Cl. ..................................... 131/335; 426/548; 426/656
[58] Field of Search ............... 131/2, 17 R, 15 R, 144, 131/12 R, 264, 9, 261 A; 260/112 R; 426/548, 656

[56] References Cited

U.S. PATENT DOCUMENTS

| 214,639 | 4/1879 | Emery | 131/144 |
| 1,784,566 | 12/1930 | Andrews | 131/264 |
| 3,006,347 | 10/1961 | Keaton | 131/17 R |
| 3,465,911 | 6/1976 | Anderson et al. | 131/2 |
| 3,998,798 | 12/1976 | Cagan et al. | 426/548 |
| 4,000,327 | 12/1976 | Tseng et al. | 131/17 R |
| 4,011,206 | 3/1977 | Higginbothom | 426/548 |
| 4,041,084 | 8/1977 | Light et al. | 131/17 R |

OTHER PUBLICATIONS

*Tobacco Flavoring for Smoking Products* by Leffingwwell et al., Pub. by R. J. Reynolds Tobacco Co., 1972, Winston Salem, NC, U.S.A. pp. 63, 17 and 58 cited.

Primary Examiner—V. Millin
Attorney, Agent, or Firm—Ostrolenk, Faber, Gerb & Soffen

[57] ABSTRACT

A tobacco-containing smoking article contains the sweet protein thaumatin and/or the sweet protein monellin at a location in the interior, whereby smoke passed to the mouth contacts the thaumatin and/or monellin. The protein is preferably out of contact with the mouth of the smoker.

13 Claims, No Drawings

SMOKING ARTICLES CONTAINING THAUMATIN OR MONELLIN

This invention relates to the use of naturally occurring protein sweeteners as flavour modifiers or enhancers for tobacco smoke.

A proteinaceous material obtained from the fruit of *Thaumatococcus daniellii*, known as thaumatin, is a potent sweetener having a sweetness of two or three orders of magnitude higher than sucrose. In the mouth, thaumatin exhibits a distinctive long-lasting sweetness coupled with a lingering aftertaste reminiscent of liquorice. Another protein sweetener, known as monellin, is obtained from the fruit of *Dioscoreophyllum cumminsii*. Monellin is about a quarter to a half as sweet as thaumatin. Various combinations of thaumatin or monellin with other sweeteners and sweetness-modifiers have been reported.

Most surprisingly, we have now found that in smoking articles such as cigarettes, incorporation of thaumatin or monellin within the article itself, preferably out of contact with the mouth, causes a distinct improvement in the flavour of the tobacco smoke, the perceived flavour being smoother and more "rounded" and less harsh, with no detectable sweetening effect.

According to the present invention, we provide a tobacco-containing smoking article, containing the sweet protein thaumatin and/or the sweet protein monellin at a location in the interior, whereby smoke passed to the mouth contacts the thaumatin and/or monellin. We also provide a method of smoothing and reducing the harshness of a tobacco-containing smoking article in which thaumatin and/or monellin is incorporated into the article at a location where it can come into contact with the smoke passing to the mouth.

The smoking article thus contains a sweet protein, namely thaumatin or monellin, impregnated in the fabric of the article. The protein may be in a position so as to come into contact with the mouth, so that the protein is actually taken into the mouth to exert its effect on the smoke flavour. However, in a preferred embodiment of the invention, the protein is in the article at a location where it does not contact the mouth. We have found that, provided the protein contacts the smoke on its way to the mouth, the desired effect is achieved. This is particularly surprising, since studies with radio-labelled protein have shown that substantially all the protein in a filter tip remains in position and is not carried to the mouth by the smoke. On average, about 95% of the protein has been found to remain in situ during the smoking of a cigarette and yet produce the desired cooling and smoothing effect on the smoke. The effect is especially noticable with American tobacco.

The smoking article may be a cigarette, cigar or pipe, and the sweet protein may be incorporated at any point in the structure of the article through which smoke passes on its way to the mouth, but which preferably is not itself in contact with the mouth. In cigarettes, the sweet protein is conveniently incorporated in the filter-tip, particularly an inner cartridge between the main filterip and the tobacco, contrasting with any use of protein in which the end of the filtertip which is inserted in the mouth is itself treated with protein. In a tobacco pipe, the protein is conveniently incorporated into a cartridge or filter to be inserted in the stem of the pipe. Small cigars, of the type having a holder or tip, can be treated in the same was as cigarettes. Larger cigars without a holder or tip, on the other hand, must have the protein incorporated internally, for example by impregnating tobacco in one end of the cigar.

The impregnation is conveniently effected using an aqueous solution. Alternatively, a dry powder, e.g. freeze-dried powder, can be incorporated in the tip and then moistened to distribute it evenly throughout. The use of a tip is preferred, as the filter medium, generally cellulose acetate, appears to adsorb the protein efficiently and the size of a conventional filter tip is sufficient for uptake of the required amount of protein. After impregnation, the article may be dried in air, preferably below 50° C.

The protein does not appear to have any useful effect when burned and therefore should preferaly be incorporated into the smoking article so that it does not come into direct contact with the burning tobacco.

We have found that the effect is produced by quite small amounts of protein. For example, a noticeable improvement in the roundness and smoothness of the tobacco smoke of a cigarette can be achieved by incorporating into the filter tip from 0.1 to 0.8 mg of thaumatin, preferably about 0.4 mg. The effect is provided by the free protein itself or by its aluminium adduct as disclosed in our British Patent Applications Nos. 17831/75 and 5719/76 (Cognate). Monellin gives a comparable effect in amounts of from 0.25 to 2.0 mg, preferably about 1.0 mg.

As a standard cigarette contains about 0.75 g of tobacco, the ratio by weight of sweet protein to tobacco is conveniently from 1:7500 to 1:940, preferaly about 1:1880 for thaumatin and from 1:3000 to 1:375, preferably about 1:750 for monellin. Accordingly, larger smoking articles should contain correspondingly larger amounts of protein. For example, a small cigar containing about 1.8 g of tobacco should preferably contain about 1 mg of thaumatin, while a slim panatella containing from 2 to 3 g of tobacco should preferably contain from 1.1 to 1.6 mg of thaumatin.

The effect was judged in blind trials in which tasters were asked to distinguish between five cigarettes, one or more of which was treated. The results were reproducible and showed that at the levels indicated thaumatin and monellin were both effective in smoothing and improving the flavour of the smoke. In comparison tests, other sweeteners such as sucrose, saccharin, dihydrochalcones and Aspartame had no effect or produced a strange or unpleasant taste. Similarly other proteins such as casein and albumen produced nauseating tastes or had no effect. Amino acids, such as glycine (itself sweet) and lysine, and polysaccharides, such as alginate, also had no effect.

We have also found that the sweet protein can extend and potentiate certain flavours. Thus, for example, incorporation of thaumatin or monellin at the above-mentioned levels into a conventional mentholated cigarette, causes the methol flavour to be increased and made longer lasting. Alternatively, the same degree of menthol flavour can be obtained by using less menthol if the protein is incorporated.

Conversely, we have also found that oil of peppermint or one of its aroma-producing components, such as menthol, can potentiate the smoothing and rounding effect of the protein, when used at levels below which its own flavour is detectable. In general, up to half the protein can be substituted by a similar weight of peppermint oil or an aromaproducing component thereof, or a mixture of the two. Thus, for example the effect of 0.4 to 0.5 mg of thaumatin in a filter tip can be obtained by using 0.2 mg of thaumatin plus 0.1 to 0.2 mg of peppermint oil or plus 0.1 mg of methanol and 0.1 mg of peppermint oil. However, 0.2 mg of thaumatin alone had a small effect and 0.2 mg of peppermint oil or menthol alone had no discernible effect at all. For comparison, it will be realised that a mentholated cigarette generally contains about 5 to 10 mg of methanol.

Thus, according to one embodiment of the present invention, we provide a cigarette containing a sweet protein as defined above, in which less than 1 mg of oil of peppermint and/or an aroma-producing component thereof is also incorporated. The cigarette advantageously contains from 0.1 to 0.4 mg of thaumatin or 0.25 to 1.0 mg of monellin, together with from 0.1 to 0.4 mg of oil of peppermint and/or one of its aroma-producing components especially menthol.

We have also found that thaumatin and monellin can be used in oral compositions such as mouthwashes, toothpastes and chewing gum to potentiate the flavour and to extend the flavour life. This effect can be obtained using levels of thaumatin below the detectable sweetness threshold so that no sweetness is being provided. Thus, for example, the flavour of chewing gum, which normally only lasts about 4 to 5 minutes, can be made to last for up to 20 minutes.

According to a further feature of the present invention, there is thus provided a method of potentiating and extending the flavour of an oral composition by adding thereto thaumatin or monellin at a level below the sweetness threshold. There is also provided a flavoured oral composition containing thaumatin or monellin at a level below the sweetness threshold.

All flavours used in such compositions are affected, for example, peppermint and spearmint and also fruit flavours. Furthermore, a cooling and smoothing effect, analogous to that obtained in smoking articles is noticeable.

The expression "sweetness threshold" is difficult to quantify in the abstract since the sweetness and other flavour characteristics of thaumatin and monellin are strongly affected by the nature of the composition, the pH and other factors. Thus, for example, solid particulate materials can adsorb the protein; surfactants can denature it; and substances such as gums can mask the flavouring effect. However, it is a simple matter to determine the threshold for any particular composition. For thaumatin we have found, for example, that for a mouthwash based on aqueous alcohol, a level of about 0.0005% by weight is the threshold and the protein is effective at levels of 0.00001 to 0.0001%, while in toothpaste containing inorganic abrasives and surfactants which affect the protein, and having a pH on the alkaline side, the threshold is as high as 0.1% and the protein is effective at levels of from 0.05 to 0.01%. Clear toothpastes containing no abrasive but some polysaccharide have threshold and effective levels about an order of 10 lower. A conventional chewing gum containing polyvinyl acetate and calcium carbonate has a threshold of about 0.05% and the protein is effective at levels of 0.01 to 0.03%. For monellin the above figures can be multiplied by a factor of about 2.5.

EXAMPLE 1

Cigarette with 2-part filter

Cigarettes were produced experimentally by cutting open conventional 2-part filter cigarettes (e.g. Embassy and Benson and Hedges) and wetting the inner part of each filter (i.e. the part which contacts the tobacco) with 0.2 ml of an aqueous solution of thaumatin (2.0 mg/ml). The treated filters were dried in a current of air and the cigarettes reassembled.

EXAMPLE 2

Cigarette with single filter

Cigarettes containing a single filter were cut open and the inner end of each filter was treated with 0.25 ml of an aqueous thaumatin solution (1.6 mg/ml). The filters were dried in a current of air and the cigarettes reassembled.

EXAMPLE 3

Examples 1 and 2 were repeated, but using solutions of monellin (4 mg/ml and 3.2 mg/ml respectively).

EXAMPLE 4

Example 1 was repeated using solutions of thaumatin (1 mg/ml) containing menthol (1 mg/ml) of peppermint oil (1 mg/ml) or a mixture of the two (each 0.5 mg/ml).

EXAMPLE 5

The outer (mouth end) part of a 2-part filter is removed and the outer surface of the inner part is moistened with 0.1 ml of water or a 0.1% by weight aqueous solution of aluminium sulphate. Powdered thaumatin (0.4 mg) was then applied to the moistened surface and the filter dried. The cigarette was then reassembled.

EXAMPLE 6

Example 5 was repeated using a 10:1 by weight dry mix of cellulose or cellulose acetate and thaumatin (4.4 mg).

EXAMPLE 7

Filter

An aqueous solution of thaumatin (2 mg/ml) is applied to extruded cellulose acetate filaments which are dried and cut into conventionally sized filter tips for cigarettes, each containing approximately 0.4 mg of thaumatin.

EXAMPLE 8

Mouthwash glycerol: 10% by weight
ethanol: 10%
cetyl pyridinium chloride: 0.05%
cinnamon and mint flavour: 0.066%
saccharin: 0.005 to 0.01%
thaumatin: 0.0001%
water: 100%

EXAMPLE 9

Chewing gum polyvinyl acetate: 20 parts by weight
butyl phethalylbutylglycolate: 3
polyisobutylene: 3
microcrystalline wax: 2
calcium carbonate: 2
flavourings: 1
saccharin: 0.1
glucose: 10
thaumatin: 0.005−0.01 (=0.0125−0.025%)

EXAMPLE 10

Toothpaste

A standard opaque toothpaste has the following composition:

dicalcium phosphate (abrasive): 50% by weight
glycerol (humectant): 30%
gum tragacanth (binder): 1%
sodium lauryl sulphate: 1%
methyl parahydroxy benzoate: 0.03%
peppermint oil: 0.04%
saccharin: 0.5%
thaumatin: 0.05%
water: to 100%

An equivalent clear paste of the conventional type (e.g. Close-Up) contains only 0.005% thaumatin because it contains less phosphate.

In the above Examples, the amount of thaumatin can be replaced by about 2.5 times the amount of monellin.

We claim:

1. A tobacco-containing smoking article, containing a sweet protein selected from the group consisting of thaumatin and monellin at a location in the interior of the article, whereby smoke passed to the mouth contacts the sweet protein, said protein being present in an amount effective to cause a perceived flavor of the article when in use without the protein to be smoother and more rounded and less harsh without being detectably sweetened thereby.

2. A smoking article according to claim 1, containing the protein at a location where it does not contact the mouth.

3. An article according to claim 1, in which the protein is located in a filter tip or filter cartridge.

4. An article according to claim 1 in which the weight ratio of sweet protein to tobacco is from 1:7500 to 1:940 for thaumatin or from 1:3000 to 1:375 for monellin.

5. An article according to claim 4 in which the weight ratio is about 1:1880 for thaumatin or about 1:750 for monellin.

6. An article according to claim 4 comprising a cigarette mentholated with at least 1 mg of menthol.

7. An article according to claim 4, in which up to half the sweet protein is substituted by a similar weight of an auxiliary additive selected from the group consisting of oil of peppermint and aroma-producing components thereof.

8. An article according to claim 7, comprising a cigarette containing from 0.1 to 0.4 mg of thaumatin or 0.25 to 1.0 mg of monellin, together with from 0.1 to 0.4 mg of said auxiliary additive.

9. An article according to claim 7, in which the said component is menthol.

10. A filter for a smoking article, comprising smoke-filtering material containing the sweet protein thaumatin or the sweet protein monellin so that smoke passing therethrough contacts said sweet protein, said protein being present in an amount effective to cause a perceived flavor of the smoke when not in contact with the protein to be smoother and more rounded and less harsh without being detectably sweetened thereby.

11. A filter according to claim 10, comprising a cigarette filter containing from about 0.1 to 0.8 mg of thaumatin or from about 0.25 to 2 mg of monellin.

12. A method of smoothing and reducing the harshness of a tobacco-containing smoking article, in which a sweet protein selected from the group consisting of thaumatin and monellin is incorporated into the article at a location where it can come into contact with smoke passing to the mouth in an amount effective to cause a perceived flavor of the article when in use without the protein to be smoother and less harsh without being detectably sweetened thereby.

13. A method according to claim 12, in which the sweet protein is located where it does not contact the mouth of the smoker.

* * * * *